United States Patent [19]

Alvarez

[11] Patent Number: 4,950,242
[45] Date of Patent: Aug. 21, 1990

[54] HYPODERMIC NEEDLE COVER AND ASSEMBLY THEREWITH

[76] Inventor: Marcial Alvarez, 220 E. Jersey St., Elizabeth, N.J. 07206

[21] Appl. No.: 407,904

[22] Filed: Sep. 15, 1989

[51] Int. Cl.$^5$ ............................................... A61M 5/00
[52] U.S. Cl. ..................................... 604/110; 604/192
[58] Field of Search ................ 604/110, 187, 192, 263

[56] References Cited

U.S. PATENT DOCUMENTS

| | | | |
|---|---|---|---|
| 4,643,722 | 2/1987 | Smith, Jr. ....................... | 604/263 X |
| 4,728,321 | 3/1988 | Chen ..................................... | 604/110 |
| 4,775,367 | 10/1988 | Schmidt .............................. | 604/192 |

Primary Examiner—John D. Yasko
Attorney, Agent, or Firm—Klauber & Jackson

[57] ABSTRACT

A cover for a hypodermic needle-syringe unit has a wall defining an elongated enclosure, a longitudinal partition divides the enclosure into a first chamber and a second chamber, the first chamber having a mouth and the second chamber having a mouth, and the second chamber containing a substance effective to clog the lumen of a hypodermic needle when the needle is brought into contact with it. Preferably, the wall covering the second chamber has a slot in it so that a hypodermic needle can be inserted into the second chamber by passing it laterally through the slot.

10 Claims, 1 Drawing Sheet

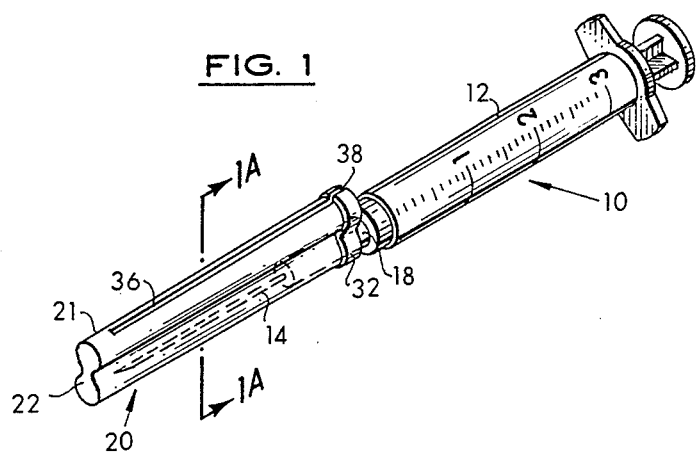
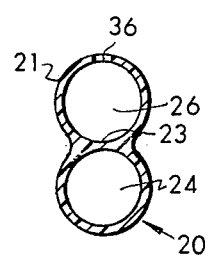
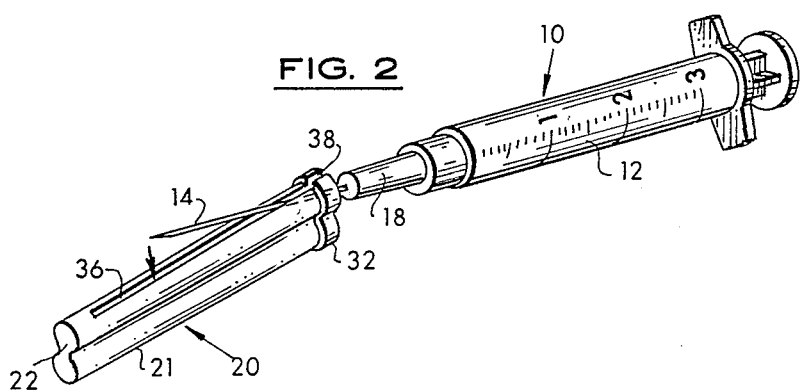
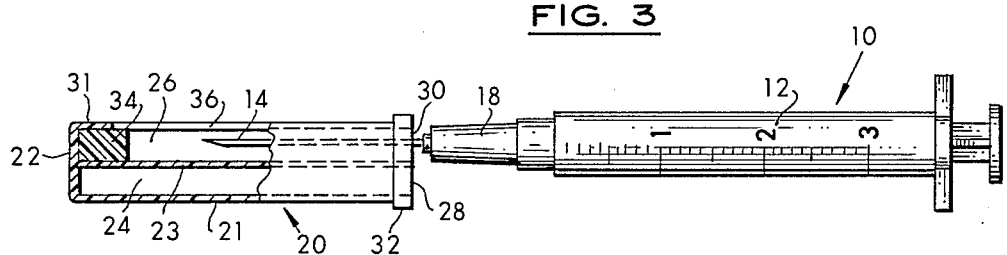
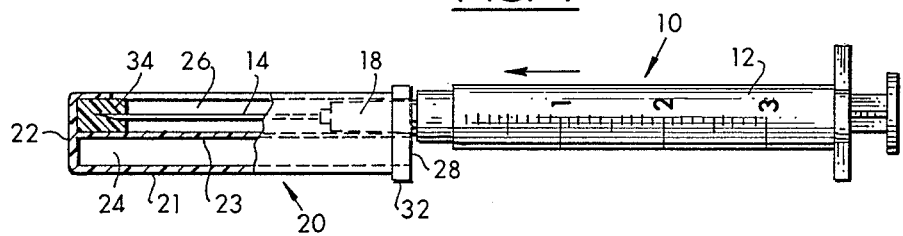

HYPODERMIC NEEDLE COVER AND ASSEMBLY THEREWITH

FIELD OF THE INVENTION

This invention relates generally to hypodermic syringe and needle apparatus, and more specifically relates to an improved covering means for the forward portion of the needle and to a disposable hypodermic needle assembly, which includes such covering.

BACKGROUND OF THE INVENTION

Within recent years, hypodermic apparatus has become widely available in the form of disposable devices or units, consisting in may instances of a syringe in association with a hypodermic needle. The hypodermic needle component of such a unit typically includes the usual hollow needle per se, together with connecting means such as a hub or the like, which enables fluid-tight connection of the needle to the syringe outlet. The entire syringe and needle unit and a cap covering the discharge end of the needle may be sealed as an "assembly" into a package or envelope which is opened at the time the hypodermic syringe and needle unit is to be used, at which time the unit is removed in a relatively sterile condition.

In common devices of the foregoing type, the syringe and needle unit often includes a relatively small, simple cylindrical cover, the open end of which frictionally engages with and is held by the hub portion of the unit. This cover is removed prior to use of the hypodermic apparatus, after which the device is filled in the usual manner by the medical practitioner, and then utilized to effect the required injection. In general, it is then contemplated that the used needle and syringe unit will be discarded, i.e. the unit, as mentioned, is deemed disposable.

In disposable devices of the aforementioned type, it has unfortunately been repeatedly found that, upon completion of the patient injection, the then uncovered hypodermic device, rather than being immediately discarded, is often placed on a table or other convenient surface. In such condition the uncovered device constitutes a serious hazard, i.e. it may continue to lie in such a position that an individual may inadvertently be injured by the exposed needle. In the event the used needle makes contact in this manner with a patient or medical attendant, not only is the danger of injury high, but moreover, since the needle has been utilized in injection of a patient, it may readily be contaminated with organisms which can effect disease transfer to the individual making contact with same. A specific danger, of course, is the well recognized possibility for thus transmitting serious diseases.

While it might be thought a simple matter to avoid these hazards by simply replacing the needle in its cover, the cover in fact is very difficult to replace because of the need to accurately guide the needle into the narrow opening defined at the mouth of the cover. Specifically the user must hold the small cylindrical cover with one hand, while accurately aiming the needle top and advancing same into the said opening. Indeed, it is all too easy for the practitioner to puncture his or her finger with the needle while trying to guide the needle back into the small cover. In one study, it was thus reported that 50% or more of needle injuries occur while recapping or disposing of needles. See R. McCormick et al. "Epidemiology of Needle Stick Injuries in Hospital Personnel". Amer. J. Med.. V. 70, April, 1981.

From time to time, proposals have been made for constructing disposable hypodermic devices of the aforementioned type as a needle assembly including a covering element which is permanent in nature but retractable. The objective of a construction of this type is partially one of assuring that the cover remains with the needle, so that there may be increased assurance that the cover will be replaced subsequent to use of the device. An example of this type of device may be seen, for example, in U.S. Pat. No. 3,134,380. An improved construction is shown in my prior U.S. Pat. No. 4,139,009. While, therefore, the advantages of a retractable cover construction have been appreciated in the prior art, the relative complexity of prior constructions has been a deterrent to their widespread use. In some cases, comparatively high cost has also been a disadvantage. Furthermore, prior devices do not prevent reuse of hypodermic needles should they be found, e.g. by drug addicts, after they have been used, with the attendant danger of the spread of disease. There is a need, therefore, for a simpler and less expensive covering for a hypodermic needle which, however, can be safely and easily employed, as well as for a covering which will preclude reuse of the needle.

OBJECT OF THE INVENTION

Pursuant to the foregoing, it may be regarded as an object of the present invention, to provide an improved covering for the discharge portion of the needle of a disposable hypodermic needle and syringe unit which cover is so constructed that it can be used in a simple yet highly effective fashion.

It is further object of the present invention, to provide apparatus of the foregoing type which includes simplified features enabling easy, positive covering of the needle.

It is still further object of the invention, to provide a disposable hypodermic needle and syringe unit with a covering for the needle such that the unit is readily adapted for use by relatively inexperienced medical practitioners, nursing personnel or the like; which device further, by virtue of its construction, tends to reduce psychological apprehension experienced by both patients and medical practitioners during and following injection of medications.

It is yet a further object of the invention to provide a cover for the needle portion of a hypodermic needle and syringe unit which includes means to occlude or otherwise clog the needle lumen after use in order to prevent its reuse.

SUMMARY OF THE INVENTION

Now, in accordance with the present invention, the foregoing objects, and others as will become apparent in the course of the ensuing specification, are achieved by a dual-chambered covering means for the forward or discharge portion of the needle of a disposable hypodermic needle and syringe assembly which includes a hypodermic syringe and needle unit, which unit may be of conventional construction.

The novel needle covering means of the invention has two adjacent but separate chambers, a first chamber for reception of the needle portion of the hypodermic needle and syringe unit before use, and a second chamber for receiving the needle portion after the hypodermic syringe and needle unit has been used for injection. It is a feature of the invention that the inner end of the second chamber contains a needle-disabling or clogging means, such as a soft rubber or plastic substance, or the like, effective to occlude or clog the needle so that it can no longer be used for its normally intended purpose.

BRIEF DESCRIPTION OF THE DRAWINGS

The foregoing objects and features of the invention will be more readily apparent from the following detailed description of illustrative embodiments and from the accompanying drawings, wherein, FIG. 1 is a perspective view of a hypodermic-needle cover embodying features of the present invention, showing it mounted in association with a conventional disposable hypodermic needle and syringe;

FIG. 1A is a transverse cross section of the assembly of FIG. 1, taken in the direction 1A—1A;

FIG. 2 is a perspective view of the novel cover in accordance with the invention, showing it being employed to receive a hypodermic needle after use;

FIG. 3 is a side elevation, partly in section, of a hypodermic needle and syringe as it is being inserted, after use into the novel cover shown in FIG. 2; and FIG. 4 is another side elevation, partly in section, of the embodiment of FIG. 3, showing the relationship of parts after the needle has been completely inserted into the novel cover.

DESCRIPTION OF THE PREFERRED EMBODIMENTS

Referring now to the drawings, and more particularly to FIG. 1 and 1A, the reference numeral 10 designates a hypodermic needle and syringe unit. Unit 10 includes a syringe 12 of generally conventional construction, to which is attached a hypodermic needle 14, also of conventional form. The syringe 12 and needle 14 are joined through a tapered end or "hub" 18 from which the needle 14 extends.

In accordance with the invention, the needle 14 is enclosed within a covering device or cap 20 of novel construction, which covers the needle and engages hub 18 of the needle-syringe unit, as seen in FIGS. 3 and 4. Covering device 20 has an outer wall 21 and a bottom 22. The wall 21 can define an enclosure of rectangular or oval cross-section, but preferably as seen in FIGS. 1 and 2, the enclosure is of a "FIG. 8" cross-section, so that the cap 20 can be easily and securely grasped by the fingers at the reduced portion of the "FIG. 8" section. The interior of covering device or cap 20 is divided longitudinally substantially along its axis by a partition wall 23 so that the cap 20 has a first chamber 24 and an adjacent second chamber 26. The chambers 24 and 26 are dimensioned to receive a conventional hypodermic needle and at the same time they have mouths 28 and 30, respectively, each of which is dimensioned to receive hub 18 of a conventional needle and syringe unit with a snug, friction fit. The mouths 28 and 30 are reinforced by a strengthening strip 32 which extends around covering device 20. When the needle 14 and syringe 12 are unused, the cap or cover 20 will be assembled with the needle 14 and the syringe 12 unit so that the needle 14 is received in the first chamber 24 and its mouth 28 will engage tapered hub 18 with a snug, friction fit to form a unified hypodermic "assembly". As mentioned, per se the syringe 12 is a conventional device, and cover 20, with such modifications as may be required to effect an appropriate interfit, can be utilized with a variety of such syringes. For purposes of concretely illustrating the present invention, however, it may be considered that syringe 12 is of a disposable plastic type, i.e. formed of such plastics as polyethylene, polyvinyl chloride (PVC), or the like. The entire assembly, i.e. syringe 12, needle 14, and cover 20 will typically be provided to the consumer, i.e. the medical practitioner, in a sealed envelope (not shown) or other package, so that the device or assembly when removed from said package is in a completely sterile condition. Since the syringe 12 and the needle 14 are, as indicated, conventional details of these particular devices are not set forth herein, and the syringe 12 and needle 14 illustrated are of conventional construction.

In accordance with the invention, second chamber 26, has at its inner end or bottom 31 a body of a needle-clogging or needle-disabling or occluding material 34. Material 34 is preferably a soft rubber or plastic putty-like substance, which is easily penetrated by the needle as to lodge in the lumen of same and thereby serve to occlude or clog the needle with such material so that the needle can no longer be used for injection.

The needle-damaging material 32 can suitably comprise a soft easily disruptible rubber such as the gum rubber commonly used in the fabrication of gum rubber erasers. Putty-like materials including plastic clays and the like are also suitable, the principal requirement being that the material readily enters and is lodgeable in the needle lumen. The material should also be relatively chemically inert and innocuous and non-toxic from a health viewpoint—so that any accidental contact of same with the medications being dispensed will not create danger to the practitioner or patient.

As seen in FIG. 2, the portion of wall 21 most remote from chamber 24 is formed with a longitudinally-extending slot 36; and strengthening strip 32, which overlies wall 22 adjacent mouths 28 and 30, is similarly formed with a cooperating slot or gap 38 to allow access to slot 36. The slots 36 and 38 permit easy insertion of needle 14 laterally into chamber 26 without the necessity of "aiming" the point of needle 14 into mouth 30.

As mentioned, when the needle-syringe cover assembly is unused or "fresh", i.e. when it is supplied in sealed, sterile condition, wrapped in a transparent flexible plastic wrapper, or the like, the cap or cover 20 is applied so that the needle 14 is received in chamber 24 with chamber mouth 28 surrounding the tapered hub 18 of the hypodermic syringe-needle unit with a snug, friction fit. To use the hypodermic unit for injection, the plastic wrapper (not shown) and cap 20 are removed and the unit is ready for use.

After use, i.e. after the injection, the needle 14 portion of the needle 14-syringe 12 unit is slipped laterally through the slot 36 in wall 21 and the slot 38 in strengthening strip 32, as illustrated in FIG. 2. This action is easily accomplished, first in that the FIG. 8 cross section facilitates holding of the cover 20; and secondly in that the user can readily initiate insertion as shown in FIG. 2 by passing the base of the needle into the slot 38 and then rotating the remainder of the needle into the remainder of slot 36. Thereupon the needle 14 is pushed forwardly into chamber 26 so that it engages and is occluded by substance 34, which disables the needle from further use. As the damaging action upon needle 14 occurs, by reason of the forward movement of needle 14, hub 18 is received in mouth 30 of chamber 26 with a snug, friction fit and cap 20 is securely held in place. The needle 14 can thus be safely covered and the needle-syringe unit is safe for disposal with needle 14 damaged so that it cannot be reused.

It will be obvious that various changes and modifications may be made in the invention without departing from the invention as defined in the appended claims. For example, the reinforcing strip 32, although preferred, can be omitted. It is intended, therefore, that all matter contained in the foregoing description and in the accompanying drawings shall be interpreted as illustrative only and not in a limiting sense.

I claim:

1. A cover for a hypodermic needle-syringe unit comprising wall means defining an elongated enclosure, a longitudinal partition dividing said enclosure into a first chamber and a second chamber, said first chamber having a mouth and said second chamber having a mouth, and means in said second chamber for disabling the discharge end of a hypodermic needle brought into contact therewith.

2. A cover as defined in claim 1, wherein the portion of said wall means enclosing said second chamber is formed with a longitudinal slot effective to guide a hypodermic needle inserted laterally therein into said second chamber following use of said needle.

3. A cover as defined in claim 1, wherein said wall means is overlain by a reinforcing strip adjacent said two mouths.

4. A cover as defined in claim 1 wherein said wall means defines an enclosure of substantially figure-eight cross-section.

5. A cover in accordance with claim 1, wherein said means for disabling said needle comprises a substance deposited at the bottom of second chamber which is effective to clog a needle inserted into same.

6. A hypodermic assembly comprising a hypodermic needle, syringe and cover for said needle, said cover comprising wall means defining an elongated enclosure, a longitudinal partition dividing said enclosure into a first chamber and a second chamber, said first chamber having a mouth and said second chamber having a mouth, and means in said second chamber for clogging the discharge end of a hypodermic needle brought into contact therewith to thereby prevent reuse of said needle.

7. As assembly as defined in claim 6, wherein the portion of said wall means enclosing said second chamber is formed with a longitudinal slot effective to guide a hypodermic needle inserted laterally therein into said second chamber.

8. As assembly as defined in claim 6, wherein said wall means is overlain by a reinforcing strip adjacent said two mouths.

9. An assembly as defined in claim 6, wherein said wall means defines an enclosure of substantially figure-eight cross-section.

10. A hypodermic assembly comprising a hypodermic needle, syringe and cover for said needle as defined in claim 6, wherein said needle and syringe are joined through a tapered hub and wherein the mouth of said first chamber engages said tapered hub with a snug, friction fit.

* * * * *